United States Patent [19]

Baldwin et al.

[11] 4,279,887
[45] Jul. 21, 1981

[54] AMIDES USEFUL AS BRAIN IMAGING AGENTS

[75] Inventors: Ronald M. Baldwin, San Francisco; Tz-Hong Lin, Fremont; Harry S. Winchell, Lafayette, all of Calif.

[73] Assignee: Medi-Physics, Inc., Emeryville, Calif.

[21] Appl. No.: 964,562

[22] Filed: Nov. 29, 1978

[51] Int. Cl.³ .............. A61K 49/00; A61K 43/00; C07C 103/37
[52] U.S. Cl. ..................... 424/1.5; 424/1; 424/9; 260/500.5 H; 564/183; 564/184
[58] Field of Search .......... 260/557 B, 558 A, 558 D, 260/558 P, 558 R, 568, 570.5 R; 424/1, 1.5, 9

[56] References Cited

U.S. PATENT DOCUMENTS

| | | | |
|---|---|---|---|
| 4,021,224 | 3/1977 | Pallos et al. | 260/558 A |
| 4,123,554 | 10/1978 | Kawada et al. | 260/558 D |
| 4,139,605 | 2/1979 | Felder et al. | 424/1.5 |

OTHER PUBLICATIONS

Tubis et al., Int. J. Appl. Rad. Isot., 15:397–400 (1964).
Elias et al., Int. J. Appl. Rad. Isot., 24:463–469 (1973).
Blau et al., Int. J. Appl. Rad. Isot., 3:217–225 (1958).
Hanson et al., J. Med. Chem., 21:830–833 (1978).
Holman et al., J. Lab. Comp. Radio Pharm., 16:69–71 (1979).

Primary Examiner—Brooks H. Hunt
Assistant Examiner—Christine M. Nucker
Attorney, Agent, or Firm—Jon S. Saxe; George M. Gould; William H. Epstein

[57] ABSTRACT

Certain radioiodine containing amides useful as brain imaging agents are disclosed. The compounds of the subject invention are represented by the formula

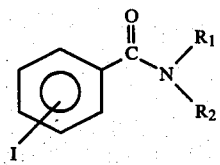

wherein I is a radioisotope of iodine with I-123 being preferred, $R_1$ and $R_2$ are the same or different and are selected from the grooup consisting of hydrogen, hydroxy, alkyl, aryl, substituted aryl, aralkyl, anilino and carbamoylmethyl or $R_1$ and $R_2$ taken together with the nitrogen to which they are attached form a 5- or 6-membered ring.

7 Claims, No Drawings

AMIDES USEFUL AS BRAIN IMAGING AGENTS

STATEMENT OF PRIOR ART

The use of radioiodine to label organic compounds for use in diagnostic nuclear medicine is well documented in the literature. Radioiodinated human serum albumin, fatty acids and triglycerides as well as ortho-iodohippuric acid have long been available for diagnostic purposes. The preparation of I-131-labeled ortho-, meta- and para-iodobenzoic acids for liver function procedures is described by Tubis et al., Int. J. Appl. Radiat. Isotopes 15, p 397 (1964).

The use of p-iodobenzoyl chloride (I-131) to label antibodies for the determination of in vivo protein distribution is reported by Blau et al., Int. J. Appl. Radiat. Isotopes 3, pp 217–225 (1958).

The use of the N-hydroxysuccinimide ester of 3-(4-hydroxyphenyl)-propionic acid-$^{125}$I to radiolabel proteins is reported by Bolton and Hunter, Biochem. J. 133 pp 529–539 (1973). Smith, U.S. Pat. No. 3,979,506, describes imido esters of radionuclide-substituted hydroxy or alkoxy phenyls wherein the nuclide can be, for example, I-125.

The art has been apprised that certain radiolabeled compounds will localize in the brain to a level sufficient to allow for imaging thereof. There has been increasing interest in finding compounds which will more effectively cross the blood/brain barrier thus facilitating more efficacious imaging of the brain.

Winstead et al, J. Nucl. Med. 16 #11, pp 1049–1057 (1975), described studies in animals indicating brain uptake of certain labeled aminonitriles. The clinical efficacy of these compounds, however, has not been established. Robinson et al, J. Nucl. Med. 17, p 1093 (1976), describe $^{123}$I-labeled 4-iodo-antipyrine as a brain imaging agent. The rapid in vivo deiodination and suboptimal concentration in the brain of this compound limit its utility.

The compounds of the subject invention are chemically distinct from those reported in the literature and they facilitate the rapid passage of a radioisotope of iodine, preferably I-123, across the blood/brain barrier. I-123 is preferred because it compares very favorably with I-131 in terms of half-life and absorbed radiation dose.

Because the half-life of I-123 is only 13 hours, it is necessary that procedures in labeling compounds with this radionuclide be both rapid and efficient. It is further necessary, as with any radiolabeled compounds, that the radiolabel, i.e. the iodine-carbon bond in the case of the subject compounds, be stable in vivo with minimal loss of radionuclide from the labeled compound after its administration to the patient. The compounds provided by the present invention satisfy all of these requirements.

DETAILED DESCRIPTION OF THE INVENTION

The present invention is directed to radioiodinated amides represented by the formula

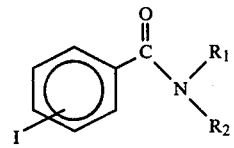

wherein I is a radioisotope of iodine and $R_1$ and $R_2$ are the same or different and are selected from the group consisting of hydrogen, hydroxy, alkyl, aryl, substituted aryl, aralkyl, anilino and carbamoylmethyl, or $R_1$ and $R_2$ taken together with the nitrogen to which they are attached form a 5- or 6-membered ring.

The compounds of formula A are useful for imaging of the brain. The compounds of the invention demonstrate rapid accumulation in the brain indicating ability to penetrate the "blood-brain barrier".

In tests in rats comparing to I-123 labeled 4-iodoantipyrine which, as mentioned above, has been described in the art by Robinson et al, J.Nucl. Med. 17, p 1093 (1976) as a brain imaging agent, the compounds of formula A demonstrate a marked superiority in stability of the iodine-carbon bond. Therefore, the compounds of formula A do not rapidly deiodinate in vivo and they demonstrate a superior localization in the brain. In addition to imaging of the brain, the compounds of formula A also demonstrate localization in the heart, the adrenals and the pancreas.

The compounds of formula A show rapid accumulation in the brain after intravenous administration without the significant loss of the iodine label in the brain which has been shown to be a disadvantage of prior art brain imaging agents such as I-123 4-iodoantipyrine. The stability of the iodine label in the brain combined with the ability to penetrate the blood/brain barrier are distinct advantages of the compounds of formula A in their use as brain imaging agents.

As utilized herein, the term "alkyl" indicates a straight-chain radical having from 1 to 18 carbon atoms such as, for example, methyl, n-propyl, n-hexyl, n-octadecyl and the like. The term "lower alkyl" denotes a straight-chain alkyl radical having from 1–6 carbon atoms. The term "aryl" as utilized herein means an aromatic, mononuclear or polynuclear hydrocarbon such as, for example, phenyl, naphthyl and phenanthryl, with phenyl being preferred. The alkyl portion of "aralkyl" as utilized herein is a straight-chain alkyl having from 1 to 6 carbon atoms. Preferred aralkyl radicals are benzyl and phenethyl.

The terminology "substituted aryl" as utilized herein indicates an aryl radical substituted with one or more lower alkyl groups, preferably 2, 6-dimethylphenyl.

In formula A wherein $R_1$ and $R_2$ together with the nitrogen to which they are attached may form a 5-or 6-membered heterocyclic ring, such rings may include an additional hetero atom selected from the group consisting of oxygen, nitrogen and sulfur. Examples of preferred groups in accordance with the invention are pyrrolidino, pyridino, piperidino, morpholino and thiomorpholino with morpholino being preferred. In formula A, I can be ortho, meta or para to the amide group with ortho being preferred.

As stated above "I" indicates all radioisotopes of iodine, e.g. I-123, I-125 and I-131. Of these I-123 is particularly preferred in the practice of the invention.

Preferred compounds in accordance with the present invention include I-123-o-iodobenzamide, I-123-N-betaphenethyl-o-iodobenzamide, I-123-N-methyl-o-iodobenzamide and I-123-N-benzyl-o-iodobenzamide.

The radioiodinated compounds of the present invention are prepared by reacting a compound represented by the formula

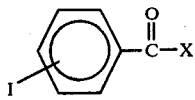

wherein I is as defined above and X is chloro, bromo or hydroxy with a compound represented by the formula

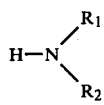

wherein $R_1$ and $R_2$ have the meanings given above.

For the above reaction the compound of formula B is conveniently dissolved in an inert organic solvent such as, for example, ethyl acetate, dioxane, methylene chloride, benzene, dimethylformamide, tetrahydrofuran and the like with the latter being preferred. The amines of formula C may be in aqueous solution if they are of low molecular weight and sufficiently soluble to do so or, in the alternative, may be in solution in an inert, organic solvent such as those named above. The reaction is usually carried out at ambient temperatures although gentle heating may be preferred in certain instances. The reaction is generally rapid requiring from about 5 minutes to about 60 minutes. The product is recovered by conventional procedures.

Alternatively, compounds of formula A wherein the I does not indicate a radioisotope of iodine; i.e., the corresponding cold compound may be prepared as described above utilizing compounds of formula B wherein I is stable iodine and not a radioisotope of iodine under the same conditions. These compounds are then exchange labeled with a radioisotope of iodine, preferably I-123.

For the exchange radiolabeling process, an inorganic salt of a radioisotope of iodine, preferably an alkali metal salt, and most preferably the sodium salt, is utilized. The salt is heated with the cold compound of formula A; i.e., a compound of formula A wherein I is stable iodine and not a radioisotope of iodine in a sealed vessel for from ¼ to about 2 hours. The exchange radiolabeling is carried out in the presence of an inert organic solvent such as, for example, a lower alcohol or those named above. The radio-labeled compound of formula A is then dissolved in a suitable solvent or vehicle and filtered through a silver chloride impregnated filter to remove unexchanged radioiodine. The exchange labeling carried out in this manner has been demonstrated to be in excess of 95%.

The compounds of formula B above can be prepared conveniently from the corresponding non-radioactive compound; i.e., a compound of formula B wherein I represents stable iodine as opposed to a radioisotope of iodine by exchange radiolabeling as described above. The cold compounds of formula B are known.

The fact that the compounds of formula A can be rapidly prepared is advantageous because of the criticality of time in the handling of radioisotopes which have a comparatively short half-life such as iodine-123.

As stated above, the radioiodine-containing compounds of the invention rapidly localize in the brain following intravenous administration. In most instances, a sufficient amount of the administered dose will accumulate in the brain within from about one to ten minutes to permit the taking of scintiphotos. The compounds of the invention will show meaningful presence in the brain for up to about 30 minutes so that significant studies may be carried out. The compounds of formula A clear the brain within a relatively short period of time and are excreted through the kidneys and bile. In addition to the brain, the compounds of formula A will also accumulate in the myocardium, adrenals and pancreas to varying degrees.

The radioiodinated compounds of the subject invention may be administered in an aqueous or aqueous/alcoholic medium. Such media may also contain conventional pharmaceutical adjunct materials such as, for example, pharmaceutically acceptable salts to adjust the osmotic pressure, buffers, preservatives and the like.

A preferred vehicle for the compounds of formula A comprises from about 20% to about 70%, preferably from about 25% to about 45%, propylene glycol, from about 1% to about 40%, preferably from about 5% to about 30%, ethanol, from about 1% to about 5% of a complexing agent such as, for example, ethylenediaminetetraacetic acid, a suitable buffer such as, for example, a mixture of acetic acid and sodium acetate, from about 0.5% to about 2% of a suitable preservative and the remainder water. Preferred preservatives include, for example, benzyl alcohol, phenol, esters of para-hydroxybenzoic acid and the like.

The following examples further illustrate the invention. Unless otherwise noted, all temperatures are in degrees centigrade.

EXAMPLE 1

A total of 40 ml of a 40% by weight aqueous solution of methylamine was reacted with a solution of 16 g of o-iodobenzoyl chloride in 25 ml of tetrahydrofuran for 10 minutes. The excess solvent was evaporated in a hot water bath at 65°. The mixture was allowed to cool and 40 ml of water was added to precipitate the crude product which was recovered and washed with 1 N NaOH, 1 N HCl, and then water until the washings were neutral. The crude product was dried under vacuum and purified by recrystallization from toluene to yield 12.6 g of N-methyl-o-iodobenzamide as white crystals, m.p. 153°–154°, $R_f$ 0.75 on thin layer chromatography using silica gel 60 and methanolchloroform-acetic acid (15:85:1) mixture.

EXAMPLE 2

A total of 50 ml of a 15 M ammonium hydroxide solution was reacted with 15 g o-iodobenzoyl chloride for 20 minutes. The crude product was recovered as in Example 1. The product was recrystallized from ethanol to yield 7.8 g of o-iodobenzamide, m.p. 187°–189°, $R_f$ 0.63.

EXAMPLE 3

Solutions of 12.2 g hexylamine and 8.0 g o-iodobenzoyl chloride in a total of 20 ml tetrahydrofuran were reacted for 10 minutes. The tetrahydrofuran was removed by heating on a water bath at 65° for 10 minutes and 50 ml of water were added to precipitate the crude product. The precipitate was recovered as in Example 1 and recrystallized from a benzene/hexane mixture as white crystals, to yield 7.6 g of N-hexyl-o-iodobenzamide, m.p. 104°–105°, $R_f$ 0.78.

EXAMPLE 4

In accordance with the procedure of Example 3, 12.1 g of cyclohexylamine was reacted with 8.0 g of o-iodobenzoyl chloride in 20 ml of tetrahydrofuran. There was obtained by recrystallization from benzene 5.7 g of fine white crystals of N-cyclohexyl-o-iodobenzamide, m.p. 148°–149°, $R_f$ 0.74.

EXAMPLE 5

A solution of 17.9 g of octadecylamine in a mixture of 300 ml of ether and 10 ml of ethanol was reacted with a solution of 8.0 g of o-iodobenzoyl chloride in 25 ml of ether for 10 minutes. The precipitate which formed contained octadecylamine hydrochloride. This precipitate was recovered and discarded. The volume was thereafter reduced to approximately half at 65° on a water bath. The resulting precipitate was recovered in accordance with the procedure of Example 3. The crude product was recrystallized from benzene to yield 1.2 g of N-octadecyl-o-iodobenzamide as a white microcrystalline solid, m.p. 94°–96°, $R_f$ 0.77.

EXAMPLE 6

In accordance with the procedure of example 3, 20 ml of aniline was reacted for one and one-half hours with 8.0 g benzoyl chloride in a total of 50 ml of ether. The excess solvent was removed by heating on a water bath at 65°; 50 ml of water and 150 ml methylene chloride was added. The organic phase was washed with 1 N HCl, and then water. The crude product, obtained by evaporating the solvent, was recrystallized from an ethanol/benzene mixture, to yield 6.7 g of o-iodobenzanilide as white crystals, m.p. 147°–148°, $R_f$ 0.79.

EXAMPLE 7

A solution of 15 ml of 2, 6-dimethylaniline in 30 ml of tetrahydrofuran was reacted with a solution of 8.0 g of o-iodobenzoyl chloride in 20 ml of tetrahydrofuran in accordance with the procedure of Example 3. There was obtained by recrystallization from a benzene/chloroform/ethanol mixture 8.1 g of o-iodobenz-2, 6-xylidide, m.p. 187°–188°, $R_f$ 0.74.

EXAMPLE 8

A solution of 15 ml of benzylamine in 20 ml of tetrahydrofuran was reacted with a solution of 8.0 g of o-iodobenzoyl chloride in 20 ml of tetrahydrofuran in accordance with the procedure of Example 3. There was obtained by recrystallization from benzene 9.1 g of N-benzyl-o-iodobenzamide, m.p. 122°–123°, $R_f$ 0.78.

EXAMPLE 9

A solution of 11.8 g phenethylamine hydrochloride in 50 ml of water was treated with 10 ml of 10 N NaOH and extracted with three 50 ml portions of ether. The combined ether extracts were washed with two 50 ml portions of water, two 50 ml portions of a saturated aqueous solution of sodium chloride, dried over sodium sulfate and filtered by gravity.

The filtrate above was reacted with a solution of 8 g of o-iodobenzoyl chloride in 25 ml of ether for 10 minutes. The ethereal solution was filtered, and the precipitate was discarded. The excess organic solvent was removed by heating on a water bath at 65° and 50 ml of water was added to precipitate the crude product, which was recovered in the manner taught in Example 3. The product was recrystallized from a benzene/hexane mixture to yield a mixture of N-phenethyl-o-iodobenzamide and o-iodobenzoic acid. This product was dissolved in 100 ml dichloromethane and washed successively with three 50 ml portions of 0.2 M NaOH, one 50 ml portion of water, three 50 ml portions of 1 M HCl, two 50 ml portions of water (until neutral) and two 50 ml portions of a saturated aqueous solution of sodium chloride, then dried over anhydrous sodium sulfate. The solution was then evaporated to dryness to yield a white solid which was recrystallized from chloroform/hexane to yield 2.1 g of N-phenethyl-o-iodobenzamide as white crystals, m.p. 125°–126°, $R_f$ 0.71.

EXAMPLE 10

A total of 25 ml of a 40% by weight aqueous solution of dimethylamine, 25 ml of tetrahydrofuran and a solution of 8 g of o-iodobenzoyl chloride in 20 ml tetrahydrofuran were reacted for 5 minutes. The tetrahydrofuran was removed by heating in a hot water bath at 65°. The crude product was obtained as a water immiscible liquid which was dissolved in 50 ml of ether and washed successively with two 30 ml portions of 1 M sodium hydrogen carbonate, two 30 ml portions of water, one 30 ml portion of 1 N hydrochloric acid, three 30 ml portions of water (until neutral) and one 30 ml portion of a saturated aqueous solution of sodium chloride, and dried over anhydrous sodium sulfate.

The ether was removed from the reaction mixture on a rotary evaporator and the resultant oil evacuated at 25° and 80 mm pressure for 24 hours, yielding 4.7 g of N, N-dimethyl-o-iodobenzamide, m.p. 33°–36°, $R_f$ 0.77.

EXAMPLE 11

A solution of 15 ml of morpholine in 30 ml of tetrahydrofuran was reacted with a solution of 8.0 g o-iodobenzoyl chloride in 20 ml tetrahydrofuran for 10 minutes. The product was obtained in the manner described in Example 3, using saturated NaCl instead of H₂O. There was obtained by recrystallization from benzene/hexane 6.8 g of N-o-iodobenzoylmorpholine as hard, translucent crystals, m.p. 86°–87°, $R_f$ 0.73.

EXAMPLE 12

A solution of 5.0 g of glycinamide hydrochloride in 10 ml of water was cooled in an ice bath during the addition of 30 ml of 6 N sodium hydroxide. To the resulting mixture was added a solution of 8.0 g o-iodobenzoyl chloride in 20 ml of tetrahydrofuran and the mixture was shaken vigorously for 2 minutes. The mixture was then stirred for 2½ hours. The tan solid which formed was filtered by suction and washed with water until the washings were neutral. The residue was then dried on a rotary evaporator for 5 hours at 60° and 80 mm Hg. There was thus obtained a crude product which was recrystallized from ethanol to yield 2.0 g of o-iodohippuramide as buff colored crystals, m.p. 183°–185°, $R_f$ 0.64.

EXAMPLE 13

A total of 10 ml of phenylhydrazine was reacted with a solution of 80 g o-iodobenzoyl chloride in 70 ml tetrahydrofuran under reflux for 2 hours. The crude product was obtained in accordance with the procedure of Example 3, and was then washed with ether, followed by 1 N HCl, and H₂O. The crude product was recrystallized from a mixture of benzene and ethanol to yield 31. g o-iodobenzphenylhydrazide, m.p. 209°–211°, $R_f$ 0.75.

EXAMPLE 14

A solution of 4.2 g of hydroxylamine hydrochloride in 20 ml of water, 30 ml of 6 N sodium hydroxide and a solution of 8.0 g of o-iodobenzoyl chloride in 20 ml tetrahydrofuran were shaken vigorously in a stoppered flask for 3 minutes, after which the mixture was stirred for 2½ hours at room temperature. The pH of the reaction mixture was adjusted to pH 7 with 13 ml of 6 N HCl and the precipitated product was collected. The product was recrystallized from ethanol to yield 3.0 g of o-iodobenzohydramic acid, m.p. 196° dec., $R_f$ 0.61. The product produced a purple color with 5% ferric chloride solution characteristic of hydroxamic acids.

EXAMPLE 15

A total of 20 ml of 15 M ammonium hydroxide was reacted with a solution of 5.4 g p-iodobenzoyl chloride in 25 ml of ether. The crude product was recovered as described in Example 3 and recrystallized from ethanol to yield 3.5 g of p-iodobenzamide as white crystals, m.p. 221°–223°, $R_f$ 0.46.

EXAMPLE 16

A total of 20 ml of a 40% aqueous solution of dimethylamine was reacted with a solution of 5.4 g p-iodobenzoyl chloride as described in Example 3 and recrystallized from a benzene/hexane mixture to yield 4.9 g N,N-dimethyl-p-iodobenzamide as white crystals, m.p. 113°–115°, $R_f$ 0.69.

EXAMPLE 17

A solution of 15 ml of morpholine in 20 ml of ether was reacted with a solution of 5.4 g p-iodobenzoyl chloride in 20 ml ether. The excess organic solvent was removed and the crude product recovered as described in Example 3. After recrystallization there was obtained 3.1 g of N-p-iodobenzoyl-morpholine as translucent crystals, m.p. 116°–117°, $R_f$ 0.72.

EXAMPLE 18

The radioiodine—containing compounds analogous to those prepared in Example 1 through 17 were prepared as follows, utilizing N-methyl-o-iodobenzamide prepared in Example 1 for illustration.

A solution of 53.7 mCi of carrier-free sodium iodide I-123 in 0.1 ml ethanol was evaporated to dryness in a test tube. A solution of 0.05 ml of 0.1 M N-methyl-o-iodobenzamide in ethanol was added and the walls of the tube were rinsed with 20 microliters of ethanol. The open end of the tube was sealed with a torch and the sealed tube heated in an autoclave at 121° for one hour.

The tube was then allowed to cool. An aliquot of the product was analyzed by thin-layer chromatography whereby it was established that the $^{123}$I-labeled compound had an $R_f$ of 0.75.

A radioactivity distribution was determined utilizing a chromatogram scanner using a sodium iodide crystal-counting system peaked to the 159 keV emission of I-123. The location of the mass of material was determined by observing the chromatogram under ultraviolet light at 254 um. As seen under the uv light, 100% of the activity was found to migrate to the above given $R_f$ which is the same as that of the starting material.

The ethanol was then evaporated to half volume and the reaction mixture taken up with a vehicle comprising a mixture of equal volumes of two solutions, the first solution comprising 50 parts ethanol, 250 parts propylene glycol and 7.5 parts benzyl alcohol, the second solution comprising 200 parts water and 50 parts of said first solution having dissolved therein 200 mg/l disodium edetate, and buffered to a pH of 7 with an acetic acid/sodium acetate buffer. The resulting solution was filtered through a bed of silver chloride prepared by passing a 2% by weight aqueous solution of silver nitrate through a filter paper disc followed by normal saline and the above described vehicle. A 3 µm membrane filter was incorporated downstream from the silver chloride impregnated disc.

EXAMPLE 19

Bioassays were performed utilizing compounds from the foregoing examples labeled with I-123 in accordance with the method described in Example 18. Female Sprague-Dawley rats weighing approximately 150 g were anesthetized with sodium pentobarbital and were injected in a tail vein with from 0.05 to 1.0 mCi (in a volume of 0.2 to 0.5 ml) of the I-123-labeled compound. Two specimens were utilized for each test.

The animals were sacrificed at 5 minutes post injection, the tails discarded and the amount of activity in various organs determined. Each organ was counted at a standardized geometry with a thallium iodide-activated sodium iodide crystal scintillation counter adjusted for the 159 keV emission of I-123. The organs were also weighed to one thousandth of a gram and the activity calculated as a percent of administered dose per gram organ weight.

The ratio of brain-to-blood activity was calculated as a percent of administered dose per gram. The results are reported in the following table. The important determinations are the amount of activity in the brain and the brain/blood ratio. The amount of activity in the stomach is related to loss of the I-123-label. For comparative purposes, I-123 antipyrine was utilized as a standard.

TABLE

| $I^{123}$-Compound Corresponding to Example No. | Percent Dose/g. at 5 min. | | | Ratio | | Percent Dose in Stomach |
|---|---|---|---|---|---|---|
| | Blood | Brain | Heart | Brain/ Blood | Heart/ Blood | |
| 1 | 0.86 | 1.04 | 1.10 | 1.21 | 1.28 | 0.94 |
| 2 | 0.69 | 0.88 | 0.91 | 1.28 | 1.32 | 0.93 |
| 3 | 0.56 | 0.59 | 1.04 | 1.05 | 1.21 | 0.86 |
| 5 | 0.91 | 0.09 | 0.84 | 0.10 | 0.92 | 0.20 |
| 6 | 0.93 | 0.84 | 2.18 | 0.90 | 2.34 | 1.66 |
| 7 | 0.69 | 0.60 | 0.99 | 0.87 | 1.43 | 0.82 |
| 8 | 0.68 | 0.68 | 1.54 | 1.00 | 2.26 | 0.88 |
| 9 | 0.43 | 0.54 | 0.73 | 1.28 | 1.70 | 0.82 |
| 10 | 2.15 | 0.48 | 1.54 | 0.22 | 0.72 | 0.93 |
| 12 | 0.84 | 0.92 | 0.96 | 1.10 | 1.31 | 0.83 |
| 13 | 1.99 | 0.39 | 1.09 | 0.20 | 0.55 | 1.10 |

| $I^{123}$-Compound Corresponding to Example No. | Percent Dose/g. at 5 min. | | | Ratio | | Percent Dose in Stomach |
| --- | --- | --- | --- | --- | --- | --- |
| | Blood | Brain | Heart | Brain/Blood | Heart/Blood | |
| 14 | 0.95 | 0.54 | 0.94 | 0.57 | 0.99 | 0.96 |
| $I^{123}$-iodoantipyrine[a] | 1.26 | 0.61 | 0.98 | 0.48 | 0.78 | 2.32 |

[a]Prepared according to J. Nucl. Med. 17, 1093 (1976).

We claim:

1. A method of imaging the brain comprising intravenously injecting an effective amount of a composition comprising a compound of the formula

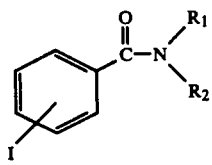

wherein I is a radioisotope of iodine, $R_1$ and $R_2$ are the same or different and are selected from the group consisting of hydrogen, hydroxy, alkyl, aryl, substituted aryl, aralkyl, anilino and carbamoylmethyl or $R_1$ and $R_2$ taken together with the nitrogen to which they are attached form a 5- or 6-membered ring, in a carrier suitable for intravenous injection and scanning the brain with a scintiscanning means.

2. A method in accordance with claim 1 wherein I is iodine-123.

3. A method in accordance with claim 1 wherein I is ortho to the amide group.

4. A method in accordance with claim 1 wherein said compound is I-123-o-iodobenzamide.

5. A method in accordance with claim 1 wherein said compound is I-123-N-beta-phenethyl-o-iodobenzamide.

6. A method in accordance with claim 1 wherein said compound is I-123-N-methyl-o-iodobenzamide.

7. A method in accordance with claim 1 wherein said compound is I-123-N-benzyl-o-iodobenzamide.

* * * * *